(12) United States Patent
Nydegger et al.

(10) Patent No.: US 8,328,849 B2
(45) Date of Patent: Dec. 11, 2012

(54) CORD FOR VERTEBRAL STABILIZATION SYSTEM

(75) Inventors: Thomas Nydegger, Thalwil (CH); Ben Alcock, Winterthur (CH); Christina Niosi, Winterthur (CH)

(73) Assignee: Zimmer GmbH, Winterthur (CH)

(*) Notice: Subject to any disclaimer, the term of this patent is extended or adjusted under 35 U.S.C. 154(b) by 276 days.

(21) Appl. No.: 12/628,343

(22) Filed: Dec. 1, 2009

(65) Prior Publication Data
US 2011/0130792 A1 Jun. 2, 2011

(51) Int. Cl.
*A61B 17/70* (2006.01)
*A61B 17/88* (2006.01)

(52) U.S. Cl. ........ 606/263; 606/254; 606/255; 606/257; 606/259; 606/279

(58) Field of Classification Search ........... 606/246–279
See application file for complete search history.

(56) References Cited

U.S. PATENT DOCUMENTS

| | | | |
|---|---|---|---|
| 3,463,158 A * | 8/1969 | Schmitt et al. ............... 606/154 |
| 4,743,260 A | 5/1988 | Burton |
| 5,176,708 A | 1/1993 | Frey et al. |
| 5,375,823 A | 12/1994 | Navas |
| 5,540,688 A | 7/1996 | Navas |
| 5,562,660 A | 10/1996 | Grob |
| 5,725,582 A | 3/1998 | Bevan et al. |
| 5,782,831 A | 7/1998 | Sherman et al. |
| RE36,221 E | 6/1999 | Breard et al. |
| 6,248,106 B1 | 6/2001 | Ferree |
| 6,290,700 B1 | 9/2001 | Schmotzer |
| 6,299,613 B1 | 10/2001 | Ogilvie et al. |
| 6,551,320 B2 | 4/2003 | Lieberman |
| 6,610,079 B1 | 8/2003 | Li et al. |
| 6,616,667 B1 | 9/2003 | Steiger et al. |

(Continued)

FOREIGN PATENT DOCUMENTS
EP 00516567 A1 12/1992
(Continued)

OTHER PUBLICATIONS

Davis, Reginald J. and Maxwell, James H., "Dynesys LIS Surgical Technique," Dynesys® LIS Less Invasive Surgery, The Dynamic Stabilization System, Zimmer Spine, Inc., Minneapolis, MN, 24 pages (2005).

(Continued)

*Primary Examiner* — Alvin Stewart
*Assistant Examiner* — Julianna N Harvey
(74) *Attorney, Agent, or Firm* — Seager Tufte & Wickhem LLC

(57) ABSTRACT

A spinal stabilization system including a cord extendable between first, second and third vertebral anchors. A first length of the cord includes a first set of intermingled filaments, and a second length of the cord includes a second set of intermingled filaments. The first set of intermingled filaments includes a first subset of filaments and a second subset of filaments, and the second set of intermingled filaments includes the first subset of filaments of the first set of intermingled filaments and a third subset of filaments different from the second subset of filaments of the first set of intermingled filaments. When secured to the first, second and third vertebral anchors, a first portion of the cord may be tensioned a first amount and a second portion of the cord may be tensioned a second amount different from the first amount.

9 Claims, 16 Drawing Sheets

U.S. PATENT DOCUMENTS

| | | | |
|---|---|---|---|
| 6,623,484 B2 | 9/2003 | Betz et al. | |
| 6,652,526 B1 | 11/2003 | Arafiles | |
| 6,802,844 B2 | 10/2004 | Ferree | |
| 6,986,771 B2 | 1/2006 | Paul et al. | |
| 6,989,011 B2 | 1/2006 | Paul et al. | |
| 7,008,424 B2 | 3/2006 | Teitelbaum | |
| 7,029,475 B2 | 4/2006 | Panjabi | |
| 7,073,415 B2 | 7/2006 | Casutt et al. | |
| 7,137,985 B2 | 11/2006 | Jahng | |
| 7,326,210 B2 | 2/2008 | Jahng et al. | |
| 7,410,489 B2 * | 8/2008 | Dakin et al. | 606/103 |
| 7,481,828 B2 | 1/2009 | Mazda et al. | |
| 7,641,673 B2 | 1/2010 | Le Couedic et al. | |
| 2002/0035366 A1 | 3/2002 | Walder et al. | |
| 2002/0083820 A1 * | 7/2002 | Greenhalgh | 87/8 |
| 2003/0220643 A1 | 11/2003 | Ferree | |
| 2004/0028872 A1 * | 2/2004 | Edwards et al. | 428/85 |
| 2004/0049189 A1 | 3/2004 | Le Couedic et al. | |
| 2004/0049190 A1 | 3/2004 | Biedermann et al. | |
| 2004/0106921 A1 | 6/2004 | Cheung et al. | |
| 2004/0143264 A1 | 7/2004 | McAfee | |
| 2004/0215191 A1 | 10/2004 | Kitchen | |
| 2004/0225289 A1 | 11/2004 | Biedermann et al. | |
| 2005/0010220 A1 | 1/2005 | Casutt et al. | |
| 2005/0056979 A1 | 3/2005 | Studer et al. | |
| 2005/0065416 A1 | 3/2005 | Subiotics | |
| 2005/0065514 A1 | 3/2005 | Studer | |
| 2005/0065516 A1 | 3/2005 | Jahng | |
| 2005/0085815 A1 | 4/2005 | Harms et al. | |
| 2005/0096652 A1 | 5/2005 | Burton | |
| 2005/0124991 A1 | 6/2005 | Jahng | |
| 2005/0143737 A1 | 6/2005 | Pafford et al. | |
| 2005/0154390 A1 | 7/2005 | Biedermann et al. | |
| 2005/0177157 A1 | 8/2005 | Jahng | |
| 2005/0203511 A1 | 9/2005 | Wilson-MacDonald et al. | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0277922 A1 | 12/2005 | Trieu et al. | |
| 2006/0047282 A1 | 3/2006 | Gordon | |
| 2006/0106380 A1 | 5/2006 | Colleran et al. | |
| 2006/0106381 A1 | 5/2006 | Ferree et al. | |
| 2006/0111715 A1 | 5/2006 | Jackson | |
| 2006/0142758 A1 | 6/2006 | Petit | |
| 2006/0173454 A1 | 8/2006 | Spitler et al. | |
| 2006/0195090 A1 | 8/2006 | Suddaby | |
| 2006/0195093 A1 | 8/2006 | Jahng | |
| 2006/0200129 A1 | 9/2006 | Denti | |
| 2006/0212033 A1 | 9/2006 | Rothman et al. | |
| 2006/0229615 A1 | 10/2006 | Abdou | |
| 2006/0247638 A1 | 11/2006 | Trieu et al. | |
| 2007/0005062 A1 | 1/2007 | Lange et al. | |
| 2007/0005063 A1 | 1/2007 | Bruneau et al. | |
| 2007/0016200 A1 | 1/2007 | Jackson | |
| 2007/0055244 A1 | 3/2007 | Jackson | |
| 2007/0100341 A1 | 5/2007 | Reglos et al. | |
| 2007/0118119 A1 | 5/2007 | Hestad | |
| 2007/0129729 A1 | 6/2007 | Petit et al. | |
| 2007/0198088 A1 | 8/2007 | Biedermann et al. | |
| 2007/0225710 A1 | 9/2007 | Jahng et al. | |
| 2007/0233075 A1 | 10/2007 | Dawson | |
| 2007/0233087 A1 | 10/2007 | Schlapfer | |
| 2007/0233095 A1 | 10/2007 | Schlaepfer | |
| 2007/0239158 A1 | 10/2007 | Trieu et al. | |
| 2007/0270821 A1 | 11/2007 | Trieu et al. | |
| 2007/0270860 A1 | 11/2007 | Jackson | |
| 2007/0293862 A1 | 12/2007 | Jackson | |
| 2008/0009863 A1 | 1/2008 | Bond et al. | |
| 2008/0021459 A1 | 1/2008 | Lim | |
| 2008/0021465 A1 | 1/2008 | Shadduck et al. | |
| 2008/0033436 A1 | 2/2008 | Song et al. | |
| 2008/0039843 A1 | 2/2008 | Abdou | |
| 2008/0051787 A1 | 2/2008 | Remington et al. | |
| 2008/0091213 A1 | 4/2008 | Jackson | |
| 2008/0140076 A1 | 6/2008 | Jackson | |
| 2008/0140133 A1 | 6/2008 | Allard et al. | |
| 2008/0140202 A1 | 6/2008 | Allard et al. | |
| 2008/0147122 A1 | 6/2008 | Jackson | |
| 2008/0154307 A1 | 6/2008 | Colleran et al. | |
| 2008/0161857 A1 | 7/2008 | Hestad et al. | |
| 2008/0177317 A1 | 7/2008 | Jackson | |
| 2008/0183216 A1 | 7/2008 | Jackson | |
| 2008/0195153 A1 | 8/2008 | Thompson | |
| 2008/0234737 A1 | 9/2008 | Boschert | |
| 2008/0234738 A1 | 9/2008 | Zylber et al. | |
| 2008/0234744 A1 | 9/2008 | Zylber et al. | |
| 2008/0262551 A1 | 10/2008 | Rice et al. | |
| 2008/0269805 A1 | 10/2008 | Dekutoski et al. | |
| 2008/0275456 A1 | 11/2008 | Vonwiller et al. | |
| 2008/0294198 A1 | 11/2008 | Jackson | |
| 2008/0300633 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1 | 1/2009 | Hestad et al. | |
| 2009/0012565 A1 | 1/2009 | Sachs et al. | |
| 2009/0030464 A1 | 1/2009 | Hestad et al. | |
| 2009/0036924 A1 | 2/2009 | Egli et al. | |
| 2009/0082815 A1 | 3/2009 | Zylber et al. | |
| 2009/0093819 A1 | 4/2009 | Joshi | |
| 2009/0093845 A1 | 4/2009 | Hestad et al. | |
| 2009/0093846 A1 | 4/2009 | Hestad | |
| 2009/0099606 A1 | 4/2009 | Hestad et al. | |
| 2009/0112265 A1 | 4/2009 | Hudgins et al. | |
| 2009/0118767 A1 | 5/2009 | Hestad et al. | |
| 2009/0198281 A1 | 8/2009 | Rice et al. | |
| 2009/0216281 A1 | 8/2009 | Vonwiller et al. | |
| 2009/0248077 A1 * | 10/2009 | Johns | 606/246 |

FOREIGN PATENT DOCUMENTS

| | | | |
|---|---|---|---|
| EP | 00669109 A1 | 8/1995 | |
| EP | 00669109 B1 | 5/1999 | |
| EP | 01523949 A1 | 4/2005 | |
| EP | 01719468 A1 | 11/2006 | |
| EP | 01523949 B1 | 6/2007 | |
| FR | 2715057 A1 | 7/1995 | |
| FR | 2775583 A1 | 9/1999 | |
| FR | 2844180 A1 | 3/2004 | |
| FR | 2867057 A1 | 9/2005 | |
| NL | 7610576 A | 3/1978 | |
| WO | WO9519149 A1 | 7/1995 | |
| WO | WO9905980 A1 | 2/1999 | |
| WO | WO9944527 A1 | 9/1999 | |
| WO | 2004024011 A1 | 3/2004 | |
| WO | 2004089244 A2 | 10/2004 | |
| WO | 2005037110 A2 | 4/2005 | |
| WO | 2005037150 A1 | 4/2005 | |
| WO | 2005087121 A1 | 9/2005 | |
| WO | 2006066685 A1 | 6/2006 | |
| WO | 2007044795 A2 | 4/2007 | |
| WO | 2007087476 A1 | 8/2007 | |
| WO | 2007109431 A3 | 1/2008 | |
| WO | 2008006098 A2 | 1/2008 | |
| WO | 2008013892 A2 | 1/2008 | |
| WO | 2008034130 A2 | 3/2008 | |
| WO | 2008021319 A2 | 8/2008 | |
| WO | 2008134703 A2 | 11/2008 | |

OTHER PUBLICATIONS

U.S. Appl. No. 12/327,710, filed Dec. 3, 2008, entitled "Cord for Vertebral Fixation Having Multiple Stiffness Phases."

U.S. Appl. No. 12/490,845, filed Jun. 24, 2009, entitled "Spinal Correction Tensioning System."

* cited by examiner

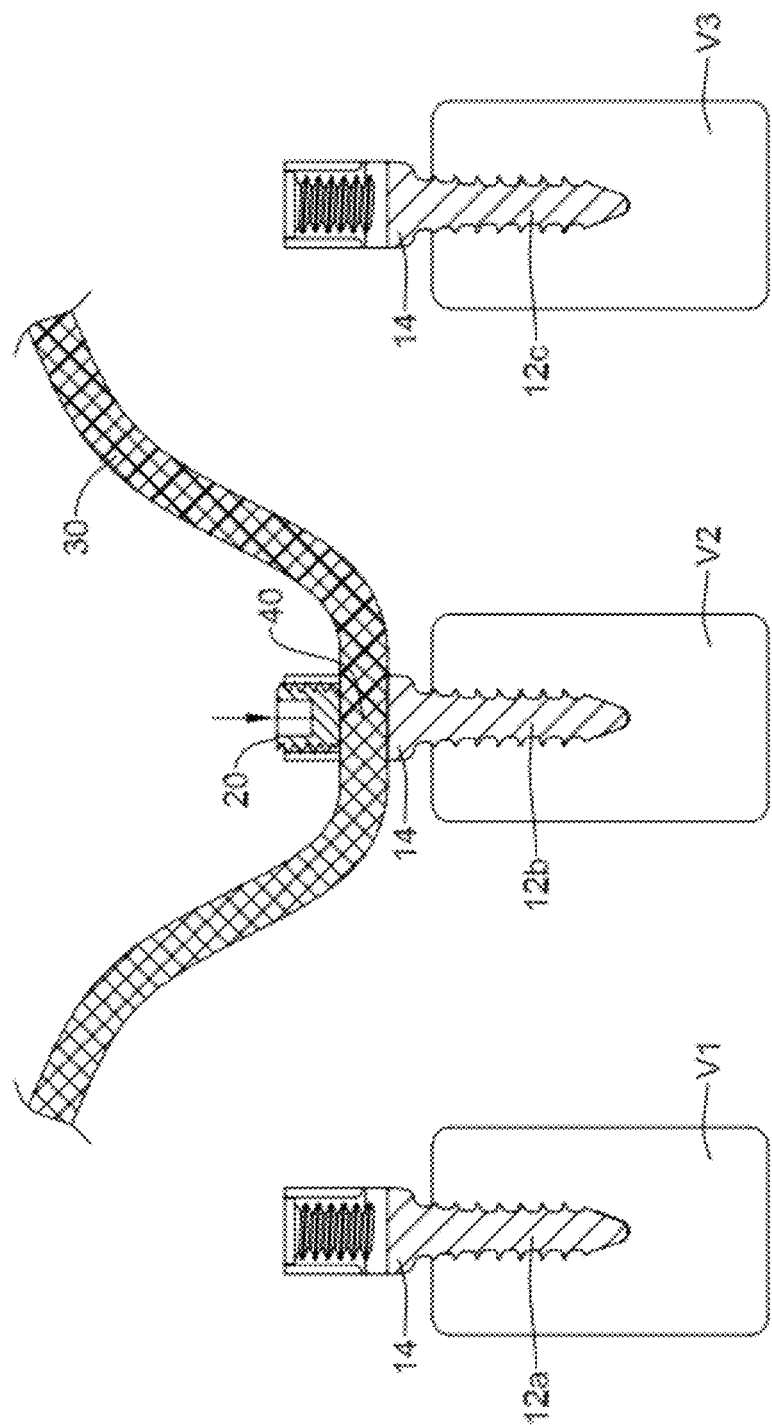

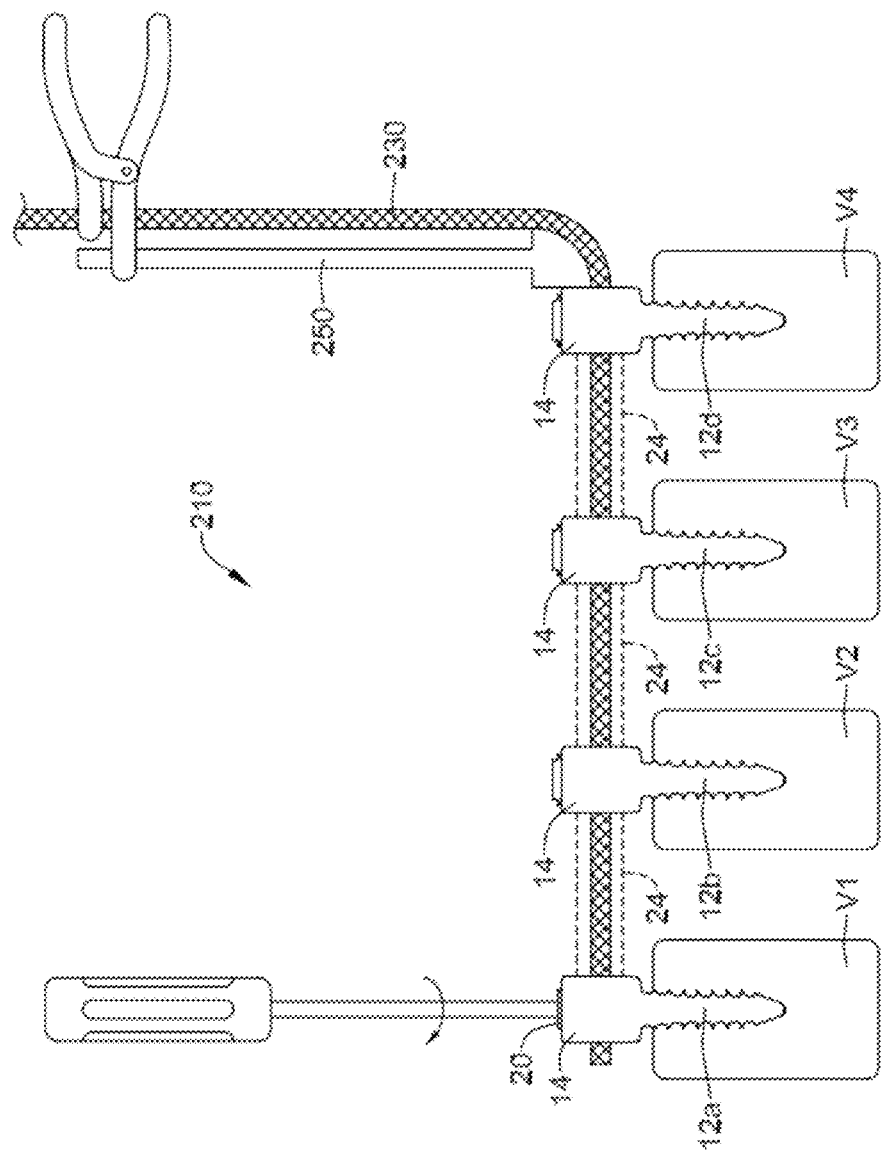

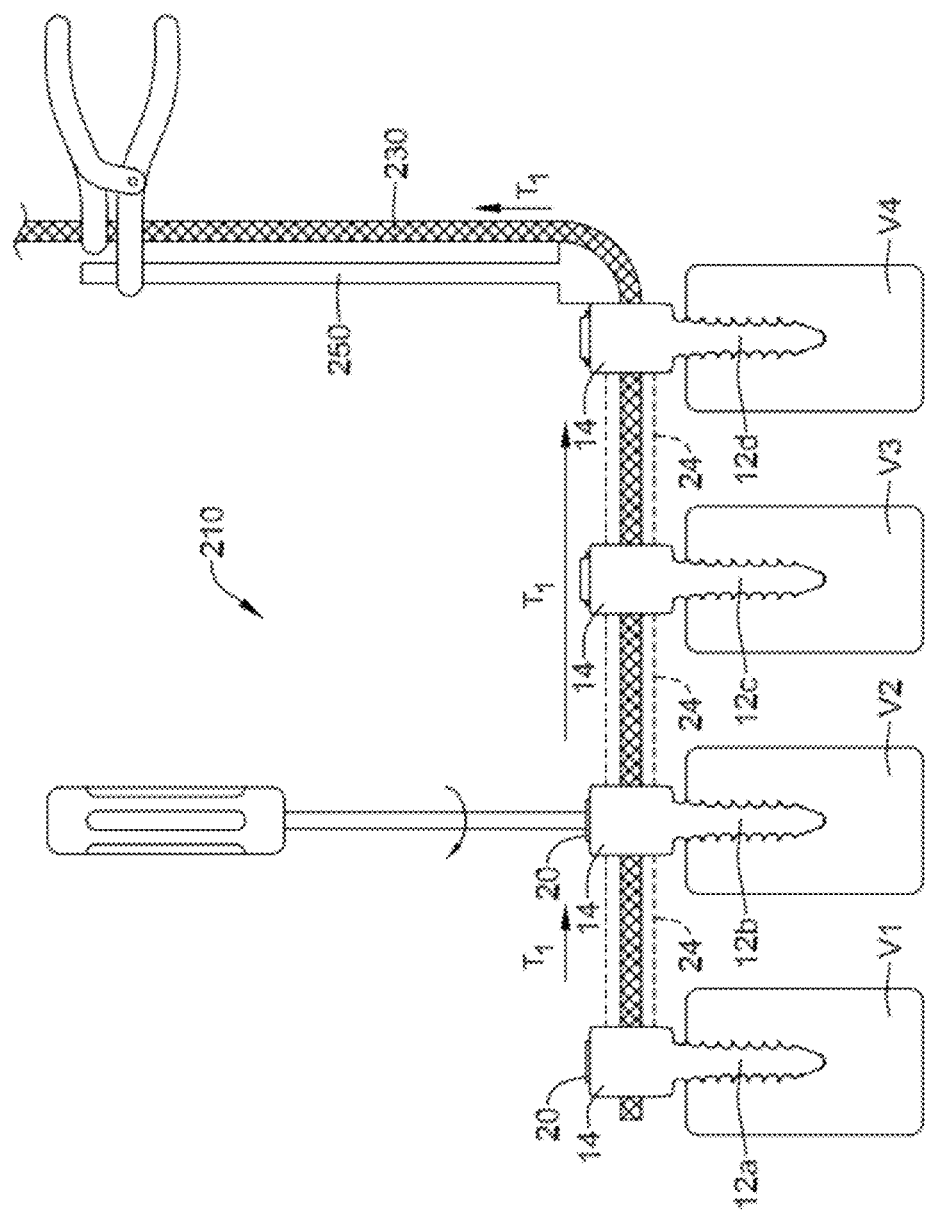

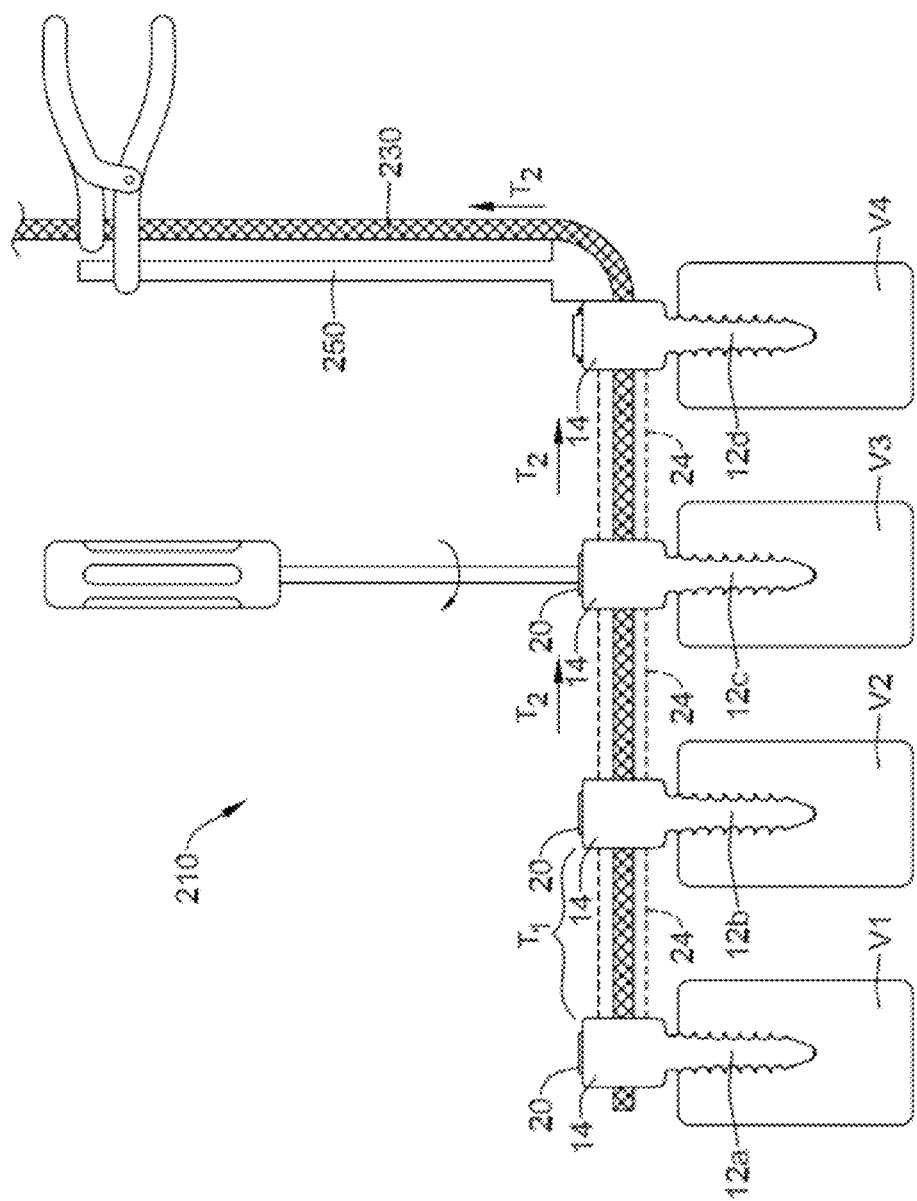

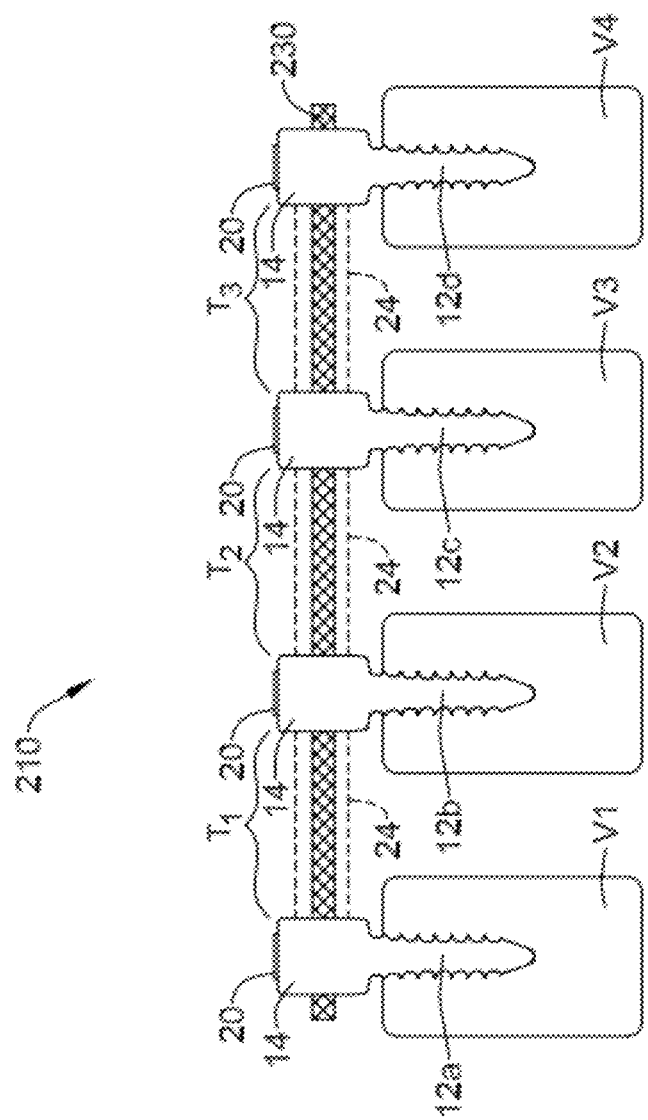

CORD FOR VERTEBRAL STABILIZATION SYSTEM

TECHNICAL FIELD

The disclosure is directed to a vertebral stabilization system. More particularly, the disclosure is directed to a characteristics, formation and/or use of a cord in a vertebral stabilization system.

BACKGROUND

The spinal column of a patient includes a plurality of vertebrae linked to one another by facet joints, ligaments and an intervertebral disc located between adjacent vertebrae. The facet joints, ligaments and intervertebral disc allow one vertebra to move relative to an adjacent vertebra, providing the spinal column with a range of motion. Diseased, degenerated, damaged, or otherwise impaired facet joints, ligaments and/or intervertebral discs may cause the patient to experience pain or discomfort and/or loss of motion, thus prompting surgery to alleviate the pain and/or restore motion of the spinal column.

Accordingly, there is an ongoing need to provide alternative devices, assemblies, systems and/or methods that can function to alleviate pain or discomfort, provide stability, such as dynamic stability, and/or restore a range of motion to a spinal segment of a spinal column.

SUMMARY

The disclosure is directed to several alternative designs, materials and methods of manufacturing medical device structures and assemblies.

Accordingly, one illustrative embodiment is a spinal stabilization system including first, second and third vertebral anchors configured to be secured to first, second and third vertebrae, respectively. The spinal stabilization system also includes a cord extendable between the first, second and third vertebral anchors. A first length of the cord includes a first set of intermingled filaments, and a second length of the cord includes a second set of intermingled filaments. The first set of intermingled filaments includes a first subset of filaments and a second subset of filaments, and the second set of intermingled filaments includes the first subset of filaments of the first set of intermingled filaments and a third subset of filaments different from the second subset of filaments of the first set of intermingled filaments.

Another illustrative embodiment is a method of forming a cord for a spinal stabilization system. The method includes forming a first length of a cord by braiding a first subset of filaments with a second subset of filaments. The second subset of filaments is substituted with a third subset of filaments different from the second subset of filaments after the first length of the cord is formed. A second length of the cord is then formed by braiding the first subset of filaments with the third subset of filaments.

Yet another illustrative embodiment is a method of stabilizing a spinal column. First, second and third vertebral anchors are secured to first, second and third vertebrae, respectively. A flexible member is secured to the first vertebral anchor and a first amount of tension is applied to a first portion of the flexible member. While maintaining the first amount of tension in the first portion of the flexible member, the flexible member is secured to the second vertebral anchor. A second amount of tension is applied to a second portion of the flexible member different from the first amount of tension. While maintaining the second amount of tension in the second portion of the flexible member, the flexible member is secured to the third vertebral anchor. With the flexible member secured to the first, second and third vertebral anchors, the first portion of the flexible member retains the first amount of tension and the second portion of the flexible member retains the second amount of tension.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIGS. 4A-4D illustrate an exemplary spinal stabilization system and method of installing the spinal stabilization system on a region of a spinal column; and FIGS. 5A-5E illustrate another exemplary spinal stabilization system and method of installing the spinal stabilization system on a region of a spinal column.

Figure 1:
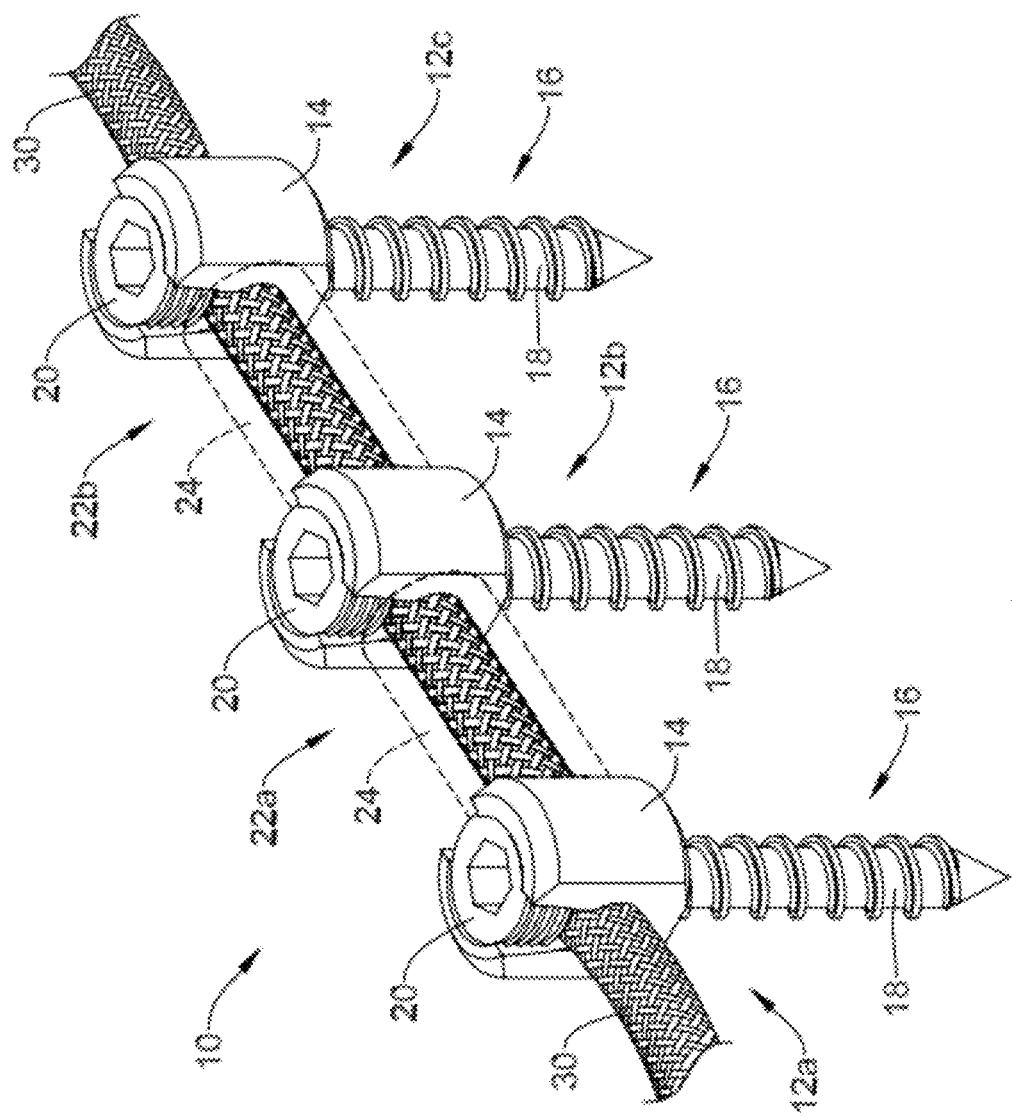
FIG. 1 is a perspective view of an exemplary vertebral stabilization system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a vertebral stabilization system 10 for stabilizing a portion of a spinal column, such as one or more spinal segments of a spinal column. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. The spinal stabilization system 10 may provide dynamic stabilization to a spinal segment, preserving and/or allowing for a range of motion of the spinal segment.

In some embodiments, the vertebral stabilization system 10 may be used to treat discogenic low back pain, degenerative spinal stenosis, disc herniations, facet syndrome, posterior element instability, adjacent level syndrome associated with spinal fusion, and/or other maladies associated with the spinal column.

The vertebral stabilization system 10 may include one or more or a plurality of vertebral anchors or fasteners 12. Although the vertebral anchors 12 are depicted as threaded vertebral fasteners (e.g., pedicle screws, bone screws), in some embodiments the vertebral anchors 12 may be vertebral hooks (e.g., laminar hooks) or other types of fastening members for attachment to a bony structure such as a vertebra of the spinal column. Each of the vertebral anchors 12 may be configured to be secured to a vertebra of a spinal column. For instance, the first vertebral anchor 12a may be secured to a first vertebra, the second vertebral anchor 12b may be secured to a second vertebra, and the third vertebral anchor 12c may be secured to a third vertebra. Additional vertebral anchors 12 may be present in instances in which the vertebral stabilization system 10 spans additional vertebrae of the spinal column.

The vertebral anchor 12 may include a head portion 14 and a bone engagement portion 16 extending from the head portion 14. In some embodiments, the bone engagement portion 16 may be a shaft portion 18 of the vertebral anchor 12 extending from the head portion 14 along a longitudinal axis of the vertebral anchor 12. In some embodiments, the vertebral anchor 12 may be a monoaxial screw, and in other embodiments the vertebral anchor 12 may be a polyaxial screw. In some embodiments, the shaft portion 18 may be configured to be installed into a bony region of a vertebra of the spinal column. For example, the shaft portion 18 may be installed into a pedicle of a vertebra, or other region of a vertebra. In some embodiments, the shaft portion 18 may be a threaded region having helical threads configured to be screwed into a pedicle of a vertebra, or other bony region of a vertebra.

The vertebral anchor 12 may include a securing element, such as a threaded fastener 20 (e.g., a set screw, cap) configured to engage the head portion 14 to secure a portion of a stabilization construct 22 to the vertebral anchor 12. For example, the threaded fastener 20 may include threads which mate with threads formed in the head portion 14.

The vertebral stabilization system 10 may also include one or more, or a plurality of stabilization constructs 22 extending between vertebral anchors 12 of the vertebral stabilization system 10. As an illustrative example, the vertebral stabilization system 10 shown in FIG. 1 includes a first stabilization construct 22a extending between the first vertebral anchor 12a and the second vertebral anchor 12b, and a second stabilization construct 22b extending between the second vertebral anchor 12b and the third vertebral anchor 12c.

The stabilization construct 22 may be constructed of a plurality of components in some instances. For instance, the stabilization construct 22 may include a spacer 24 (shown in phantom lines), and a cord 30 extending through the spacer 24, as well as other components if desired. In some embodiments, the first and second stabilization constructs 22a, 22b may utilize first and second portions, respectively, of the cord 30.

In some embodiments, the spacer 24 may be an annular spacer having a lumen (not shown) extending from a first end to a second end of the spacer 24. For example, in some embodiments the spacer 24 may be a cylindrical member having a lumen extending therethrough. In other embodiments, the spacer 24 may be molded, extruded, or otherwise formed over and/or around the cord 30. A spacer 24 may be positioned between the head portion 14 of the first vertebral anchor 12a and the head portion 14 of the second vertebral anchor 12b, and another spacer 24 may be positioned between the head portion 14 of the second vertebral anchor 12b and the third vertebral anchor 12c.

The cord 30 may extend from the head portion 14 of the first vertebral anchor 12a to the head portion 14 of the third vertebral anchor 12c, while passing through the head portion 14 of the second vertebral anchor 12b. In some embodiments, the cord 30 may extend into and/or extend through a channel, such as a U-shaped channel, extending through the head portion 14 of the first vertebral anchor 12a, the cord 30 may extend into and/or extend through a channel, such as a U-shaped channel, extending through the head portion 14 of the second vertebral anchor 12b, and the cord 30 may extend into and/or through a channel, such as a U-shaped channel, extending through the head portion 14 of the third vertebral anchor 12c. In some embodiments, the threaded fastener 20 of the first vertebral anchor 12a may be tightened directly onto the cord 30 to retain the cord 30 in the channel of the head portion 14 of the first vertebral anchor 12a, the threaded fastener 20 of the second vertebral anchor 12b may be tightened directly onto the cord 30 to retain the cord 30 in the channel of the head portion 14 of the second vertebral anchor 12b, and/or the threaded fastener 20 of the third vertebral anchor 12c may be tightened directly onto the cord 30 to retain the cord 30 in the channel of the head portion 14 of the third vertebral anchor 12c. In other embodiments, the cord 30 may extend into, extend through, and/or be secured to another component which spaces the cord 30 from direct contact with the channel of the vertebral anchor 12a, 12b, 12c and/or the threaded fastener 20 or other securing fastener For example, the cord 30 may extend into, extend through, and/or be secured to a spindle, spool, sleeve, coupler, or other component, which in turn is secured in the channel of the head portion of the vertebral anchor 12a, 12b, 12c with the threaded fastener 20 or other securing fastener. It is noted that during a medical procedure the end portions of the cord 30 which are shown extending from the channels of the vertebral anchors 12a, 12c may be trimmed as desired to reduce and/or eliminate the portion of the cord 30 extending from the vertebral anchors 12a, 12c.

When implanted in a patient, the cord 30 of the vertebral stabilization system 10 may limit the range of flexion of the spinal segment, whereas the spacer 24 may limit the range of extension of the spinal segment. In lateral bending and axial rotation, the cord 30 and/or the spacer 24 may limit the range of motion by interacting with each other in a combination of compression, shear and tensile loading. For instance, the cord 30 may be placed in tension and the spacer 24 may be placed in compression between the vertebral anchors 12a, 12b, 12c.

Figure 2:
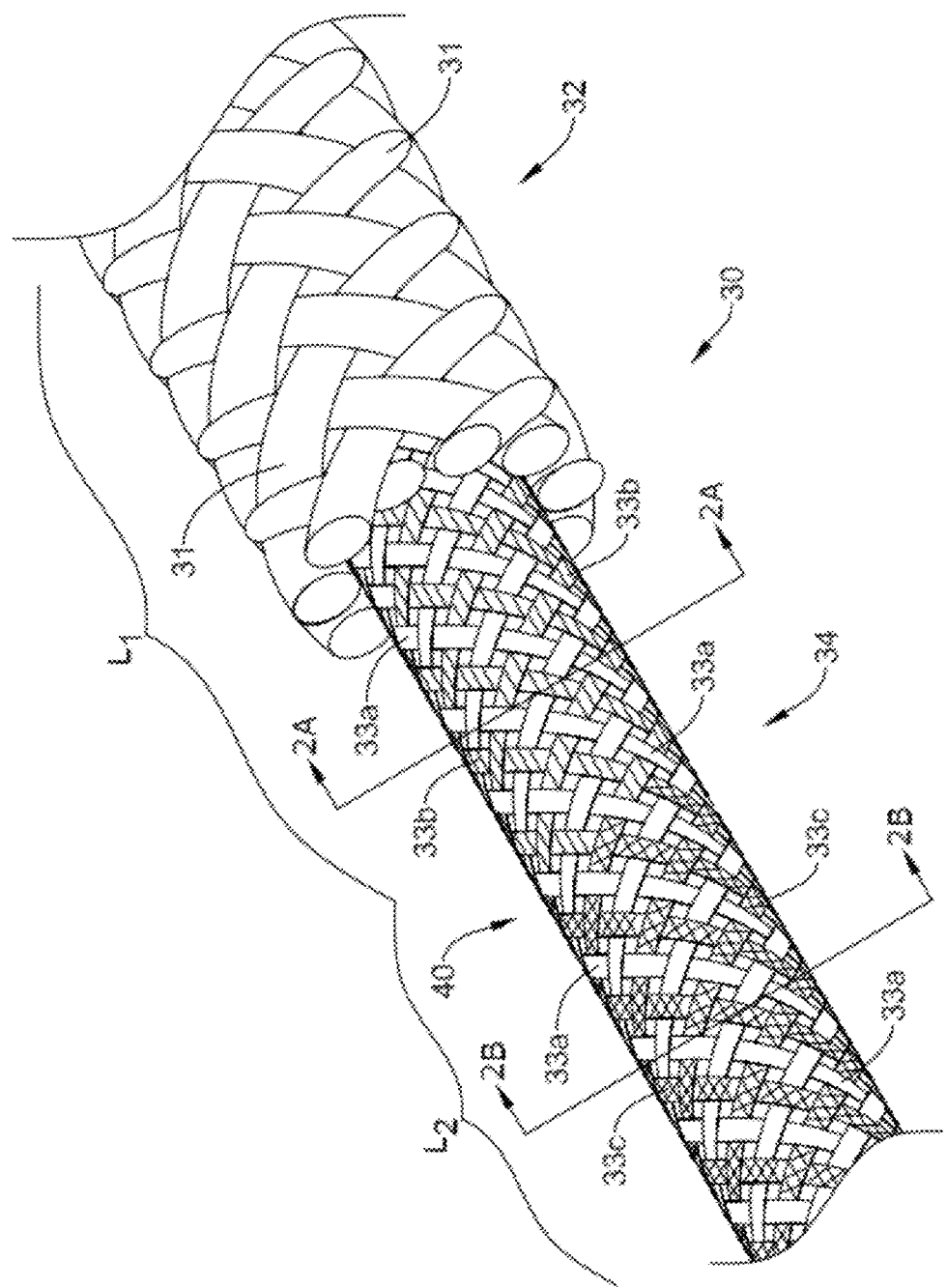
FIG. 2 is a perspective view of one embodiment of the cord of the vertebral stabilization system.

One exemplary embodiment of the cord 30 is illustrated in FIG. 2. The cord 30 may include a plurality of filaments 31 forming an outer layer 32 of the cord 30, and the cord 30 may include a plurality of filaments 33 forming an inner layer 34 of the cord 30. The inner layer 34 of the cord 30 is located within the outer layer 32 of the cord 30, and in some embodiments may be an innermost layer of the cord 30. In other embodiments, the cord 30 may include one or more additional layers located within the inner layer 34. For example, the cord 30 may include a central layer or core layer located within the inner layer 34. The outer layer 32 of the cord 30 is located exterior of the inner layer 34, and in some embodiments may be an outermost layer of the cord 30. In other embodiments, the cord 30 may include one or more additional layers located exterior of the outer layer 32, such as a braid layer, a coating, a jacket, a sleeve, or other layer of material.

The plurality of filaments 33 forming the inner layer 34 may be braided, woven, knitted, twisted or otherwise intermingled to form the inner layer 34 in some embodiments. Thus, in some embodiments the inner layer 34 may be a braided, woven, knitted, or twisted layer of the cord 30. The inner layer 34 may include any desired number of filaments 33. For example, the inner layer 34 may include 1, 2, 4, 8, 16, 20, 24, 28, or 32 filaments 33 in some instances.

The cord 30 may include a first length $L_1$ having physical characteristics different from one or more additional lengths of the cord 30, such as a second length $L_2$ of the cord 30. For instance, the first length $L_1$ of the cord 30 may exhibit a first amount of elongation per unit of applied tensile force and the second length $L_2$ of the cord 30 may exhibit a second amount of elongation per unit of applied tensile force. In some instances, the first length $L_1$ of the cord 30 may have a first stiffness and the second length $L_2$ of the cord 30 may have a second stiffness different from the first stiffness. As used herein, the term stiffness of the cord 30 is intended to refer to the tensile force (i.e., load) divided by the displacement of the cord 30 subjected to the applied tensile force. Thus, stiffness (e.g., N/mm) equals force (e.g., Newtons) divided by elongation (e.g., millimeters). In some embodiments, the cord 30 may include a third length exhibiting a third amount of elongation per unit of applied tensile force different from the first length $L_1$ and/or the second length $L_2$. In some embodiments, the cord 30 may include a third length exhibiting a third stiffness different from the first length $L_1$ and/or the second length $L_2$. The first length $L_1$ of the cord 30 may include a first set of intermingled filaments 33 and the second length $L_2$ of the cord 30 may include a second set of intermingled filaments 33.

In some embodiments, as shown in FIG. 2, the first set of intermingled filaments 33 of the inner layer 34, forming the first length $L_1$, may include a first subset of filaments 33a and a second subset of filaments 33b. The first subset of filaments 33a may have an elasticity similar to or different from the elasticity of the second subset of filaments 33b. In some instances the first subset of filaments 33a may be formed of the same material or a different material from the second subset of filaments 33b.

For instance, the first subset of filaments 33a and/or the second subset of filaments 33b may be considered a stiff, load bearing component of the inner layer 34 of the cord 30. As such, the filaments 33a, 33b, which may be referred to as stiff reinforcement filaments, may be formed of a material exhibiting strong, stiff characteristics having low elastic elongation. For instance, the material of the stiff reinforcement filaments 33a, 33b, which may be a polymer in some cases, may have a tensile strength of more than 100 MPa, preferably more than 500 MPa, and a tensile modulus of elasticity (Young's Modulus) of more than 1 GPa, preferably more than 3 GPa. Some suitable materials for the stiff reinforcement filaments 33a, 33b include, but are not limited to, polyethylene terephthalate, polybutylene terephthalate, polyethylene naphthalate, polyethylene, polypropylene, polyethylene oxide, polyethylene glycol, polypropylene oxide, polyoxymethylene, polytetrafluoroethylene, polyurethane, polyetherurethane, polycarbonate urethane, polyamide, polyimide, polyetherimide, polyetheretherketone, polyaryletherketone, polyvinylchloride, polystyrene, polycarbonate, polyphenylsulfone, polysulfone, acrylics, silicones and copolymers, blends or combinations thereof.

In some embodiments in which the first length $L_1$ of the inner layer 34 is formed solely of filaments of one desired material, the first subset of filaments 33a and the second subset of filaments 33b of the inner layer 34 may be stiff filaments formed of a stiff material such as one of the materials listed above, or other desired material.

Additionally or alternatively, the first subset of filaments 33a and/or the second subset of filaments 33b may be considered a more compliant, elastic component of the inner layer 34 of the cord 30. As such, the filaments 33a, 33b, which may be referred to as elastic filaments, may be formed of a material exhibiting high elastic recovery and low plastic deformation. For instance, the material of the elastic filaments 33a, 33b, which may be a polymer in some cases, may have a tensile strength of more than 100 MPa, preferably more than 500 MPa, and a tensile modulus of elasticity (Young's Modulus) of less than 1 GPa. Some suitable materials for the elastic filaments 33a, 33b include, but are not limited to, thermoplastic polyurethanes (e.g., polycarbonate urethane, polyetherurethane), polyetheresters, polyetherethers, polyolefinic elastomers, EPM (ethylene propylene rubber), EPDM rubber (ethylene propylene diene rubber), epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers, thermoplastic vulcanizates, thermoplastic olefins (e.g., syndiotactic polypropylene), polysulfide rubber and copolymers, blends or combinations thereof.

In some embodiments in which the first length $L_1$ of the inner layer 34 is formed solely of filaments of one desired material, the first subset of filaments 33a and the second subset of filaments 33b of the inner layer 34 may be elastic filaments formed of an elastic material such as one of the materials listed above or other desired material.

The first subset of filaments 33a and the second subset of filaments 33b may be included in the first length $L_1$ of the inner layer 34 in any desired proportions as needed to attain the desired mechanical requirements of the first length $L_1$ of the cord 30. For instance, there may be an equivalent number of the first subset of filaments 33a to the number of the second subset of filaments 33b in the first length $L_1$ of the inner layer 34 in some embodiments. In other embodiments, the first subset of filaments 33a may make up a majority of or all of the filaments of the first length $L_1$ of the inner layer 34 and the second subset of filaments 33b may make up a minority of or none of the filaments of the first length $L_1$ of the inner layer 34. In yet other embodiments, the first subset of filaments 33a may make up a minority of or none of the filaments of the first length $L_1$ of the inner layer 34 and the second subset of filaments 33b may make up a majority of or all of the filaments of the first length $L_1$ of the inner layer 34.

In some embodiments, as shown in FIG. 2, the second set of intermingled filaments 33 of the inner layer 34, forming the second length $L_2$, may include at least a portion of or all of the first subset of filaments 33a of the first set of intermingled filaments 33 and a third subset of filaments 33c. The third subset of filaments 33c may be substituted for the second subset of filaments 33b, or a portion thereof. The third subset of filaments 33c may have an elasticity similar to or different from the elasticity of the first subset of filaments 33a and/or the second subset of filaments 33b. In some instances the first subset of filaments 33a may be formed of the same material or a different material from the third subset of filaments 33c.

For instance, third subset of filaments 33c may be considered a stiff, load bearing component of the second length $L_2$ of the inner layer 34 of the cord 30. As such, the filaments 33c, which may be referred to as stiff reinforcement filaments, may be formed of a material exhibiting strong, stiff characteristics having low elastic elongation. For instance, the third subset of filaments 33c may be stiff filaments formed of a stiff material such as one of the materials listed above, or other desired material.

In some embodiments in which the second length $L_2$ of the inner layer 34 is formed solely of filaments of one desired material, the first subset of filaments 33a and the third subset of filaments 33c of the inner layer 34 may be stiff filaments formed of a stiff material such as one of the materials listed above, or other desired material.

Additionally or alternatively, the third subset of filaments 33c may be considered a more compliant, elastic component of the second length $L_2$ of the inner layer 34 of the cord 30. As such, the filaments 33c, which may be referred to as elastic filaments, may be formed of a material exhibiting high elastic recovery and low plastic deformation. For instance, the third subset of filament 33c may be elastic filaments formed of an elastic material such as one of the materials listed above or other desired material.

In some embodiments in which the second length $L_2$ of the inner layer 34 is formed solely of filaments of one desired material, the first subset of filaments 33a and the third subset of filaments 33c of the inner layer 34 may be elastic filaments formed of an elastic material such as one of the materials listed above or other desired material.

The first subset of filaments 33a and the third subset of filaments 33c may be included in the second length $L_2$ of the inner layer 34 in any desired proportions as needed to attain the desired mechanical requirements of the second length $L_2$ of the cord 30. For instance, there may be an equivalent number of the first subset of filaments 33a to the number of the third subset of filaments 33c in the second length $L_2$ of the inner layer 34 in some embodiments. In other embodiments, the first subset of filaments 33a may make up a majority of or all of the filaments of the second length $L_2$ of the inner layer 34 and the third subset of filaments 33c may make up a minority of or none of the filaments of the second length $L_2$ of the inner layer 34. In yet other embodiments, the first subset of filaments 33a may make up a minority of or none of the filaments of the second length $L_2$ of the inner layer 34 and the third subset of filaments 33c may make up a majority of or all of the filaments of the second length $L_2$ of the inner layer 34.

In some instances, the first length $L_1$ of the cord 30 may be devoid of the third subset of filaments 33c and/or the second length $L_2$ of the cord 30 may be devoid of the second subset of filaments 33b. In other embodiments, the third subset of filaments may be included in the second length $L_2$ of the cord 30 along with at least a portion of the first subset of filaments 33a and/or at least a portion of the second subset of filaments 33b of the first length $L_1$ of the cord 30. In other embodiments, at least a portion of the first subset of filaments 33a and/or at least a portion of the second subset of filaments 33b of the first length $L_1$ of the cord 30 may eliminated from the second length $L_2$ of the cord 30 without being replaced by additional filaments 33.

A transition region 40 may be defined between the first length $L_1$ and the second length $L_2$ of the cord 30. The transition region 40 may be a region where ends of the third subset of filaments 33c are located. Additionally or alternatively, the transition region 40 may be a region where ends of the second subset of filaments 33b are located. In some instances, ends of the second subset of filaments 33b are adjacent ends of the third subset of filaments 33c at the transition region 40. The ends of the second subset of filaments 33b may or may not be coupled, bonded, or affixed to the ends of the second subset of filaments 33c. In some instances ends of the second subset of filaments 33b may abut or overlap ends of the third subset of filaments 33c.

In some instances, the first length $L_1$ and/or the second length $L_2$ of the cord 30 may have characteristics similar to the cord disclosed in U.S. application Ser. No. 12/327,710, filed Dec. 3, 2008, entitled "Cord for Vertebral Fixation Having Multiple Stiffness Phases", incorporated herein by reference. In some instances, the cord 30 may include a third length in which at least a portion of the first subset of filaments 33a, the second subset of filaments 33b, and/or the third subset of filaments 33 is substituted with a fourth subset of filaments. For instance, the fourth subset of filaments may be intermingled with at least a portion of the first subset of filaments 33a, the second subset of filaments 33b, and/or the third subset of filaments throughout a third length of the cord 30.

In some embodiments the first length $L_1$ of the cord 30 may additionally or alternatively include other characteristics dissimilar to the second length $L_2$ of the cord 30. For instance, the first length $L_1$ may include filaments 33 of a different size, shape, quantity, pitch, or other arrangement than the filaments 33 of the second length $L_2$.

The plurality of filaments 31 forming the outer layer 32 may be braided, woven, knitted, twisted or otherwise intermingled to form the outer layer 32 in some embodiments. Thus, in some embodiments the outer layer 32 may be a braided, woven, knitted, or twisted layer of the cord 30. The outer layer 32 may include any desired number of filaments 31. For example, the outer layer 32 may include 1, 2, 4, 8, 16, 20, 24, 28, or 32 filaments 31 in some instances. In other instances, the outer layer 32 may be a solid tubular member or jacket disposed over the inner layer 34.

The filaments 31 may be formed of any of the materials listed above, including those described as stiff filaments and/or those described as elastic filaments, or other desired materials. In some embodiments, each of the filaments of the outer layer 32 may be formed of a single material, while in other embodiments the outer layer 32 may be formed of multiple filaments of two or more different materials. For example, in some embodiments, the outer layer 32, which may be a braided outermost layer of the cord 30, may be formed solely of polyethylene terephthalate (PET) filaments. It is thought that an outermost layer including only braided polyethylene terephthalate (PET) filaments may be beneficial for abrasion resistance.

Although in the illustrated embodiment shown in FIG. 2, a portion of the filaments 33 of the inner layer 34 are substituted or exchanged for filaments 33 having dissimilar characteristics along different lengths of the cord 30, in some embodiments, a portion of the filaments 31 of the outer layer 32 may be substituted or exchanged in a similar fashion.

Figure 2A:
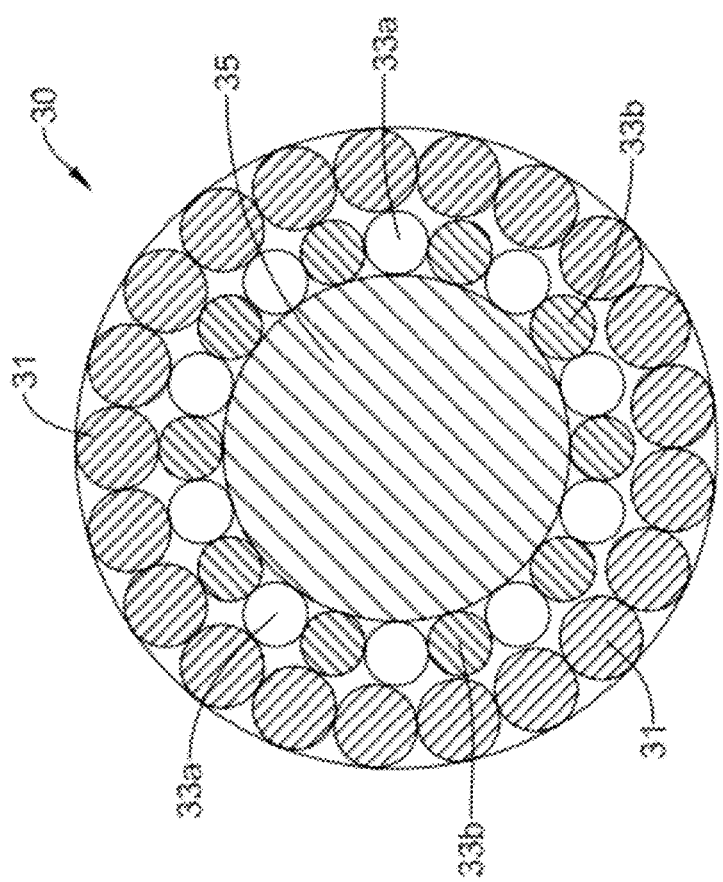
FIG. 2A is a transverse cross-sectional view of the cord of FIG. 2 taken along line 2A-2A.
Figure 2B:
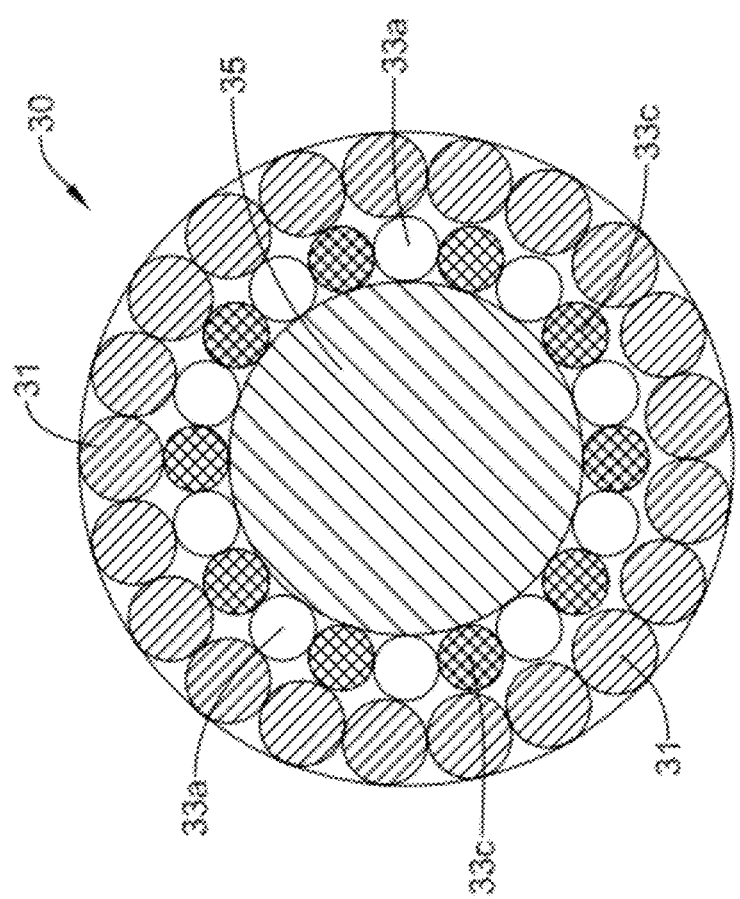
FIG. 2B is a transverse cross-sectional view of the cord of FIG. 2 taken along line 2B-2B.

FIGS. 2A and 2B are cross-sectional views of the cord 30 taken across the first length $L_1$ and the second length $L_2$, respectively, of the cord 30, including the outer layer 32, which has been truncated in FIG. 2 to better illustrate the first length $L_1$, the second length $L_2$ and the transition region 40 of the inner layer 34. It is noted, however, that the outer layer 32 may be disposed over the first length $L_1$, the second length $L_2$ and the transition region 40.

As shown in FIGS. 2A and 2B, in some embodiments, the cord 30 may include a core 35 extending through the inner layer 34. In some embodiments, the core 35 may include a piece of material, such as one or more strands or filaments of material, extending axially through the cord 30. In other embodiments, the core 35 may include a plurality of strands or filaments of material extending along the central axis of the cord 30 in a twisted, braided, woven, or otherwise intermingled fashion. The core 35 may be formed of any of the materials listed above, or other desired materials.

Figure 3A:
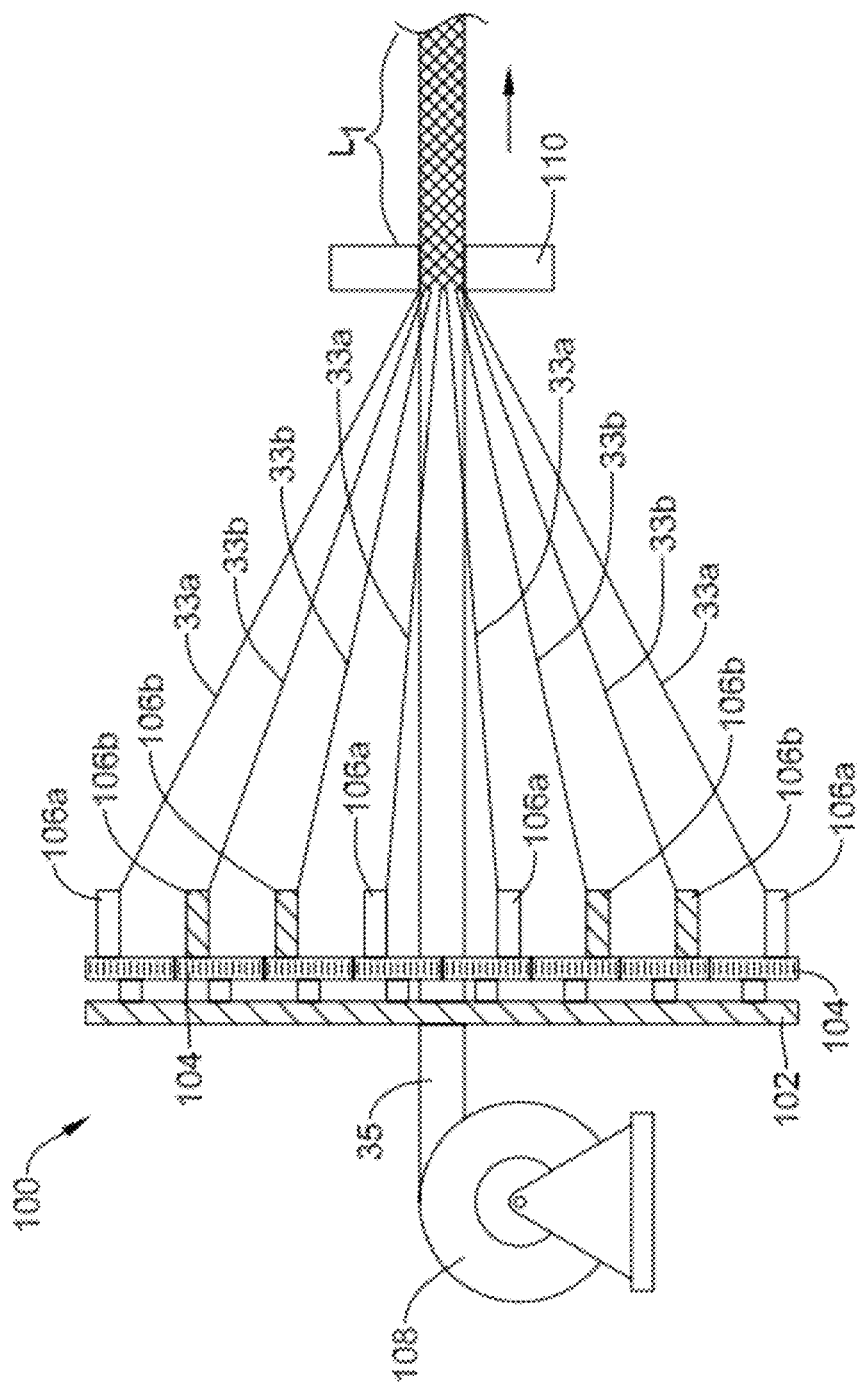
FIGS. 3A-3C illustrate an exemplary process of constructing a cord for use in a vertebral stabilization system.
Figure 3B:
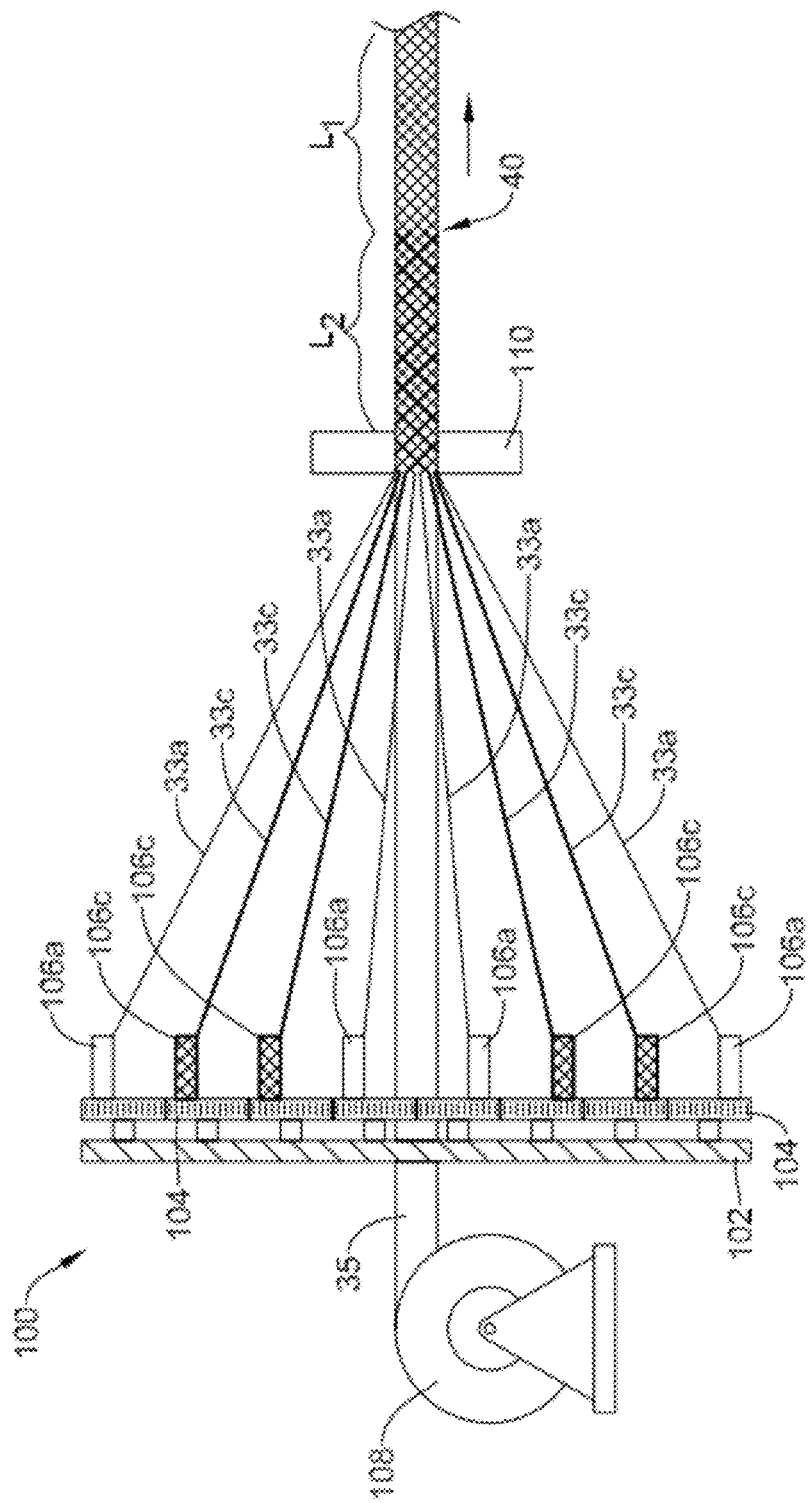
Figure 3C:
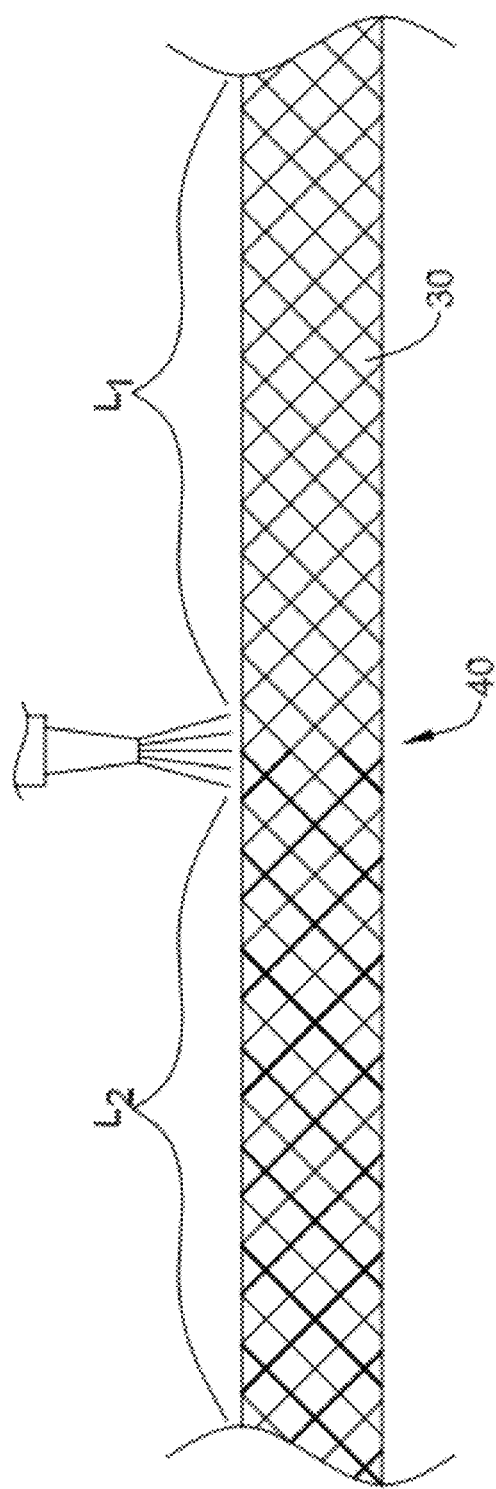

FIGS. 3A through 3C illustrate an exemplary method of forming the cord 30. A braiding machine 100 is schematically depicted in FIGS. 3A and 3B. The term braiding machine 100 includes machines designed to braid, weave, knit, twist or otherwise intermingle multiple filaments 33 to form a multifilar construct. The braiding machine 100 includes a support 102 onto which a plurality of gears 104 are rotatably mounted. A spool or bobbin 106 is associated with each gear 104, for dispensing a filament 33 in forming the cord 30. Although eight spools 106, dispensing eight filaments 33, are depicted in the figures, it is understood that the braiding machine 100 may be equipped to dispense any number of filaments 33, as desired, to form a desired cord 30.

As shown in FIG. 3A, a first length $L_1$ of the cord 30 may be formed by intermingling a first subset of filaments 33a, dispensed from associated spools 106a, with a second subset of filaments 33b, dispensed from associated spools 106b, over a core 35 dispensed off a pay out reel 108. The filaments 33 may be formed into a braided, woven, knitted or twisted construct as the cord 30 passes through a die plate 110 of the braiding machine 100.

Once the first length $L_1$ of the cord 30 has been formed, the second subset of filaments 33b and associated spools 106b may be substituted or exchanged with a third subset of filaments 33c and associated spools 106c. As shown in FIG. 3B, a second length $L_2$ of the cord 30 may then be formed by intermingling the first subset of filaments 33a, dispensed from associated spools 106a, with a third subset of filaments 33c, dispensed from associated spools 106c, over the core 35 dispensed off a pay out reel 108. If desired, additional lengths of the cord 30 may be formed by substituting a fourth subset of filaments and associated spools for at least a portion of the first subset of filaments 33a and/or at least a portion of the third subset of filaments 33c in a similar fashion.

The resultant cord 30 may include a transition region 40 located between the first length $L_1$ and the second length $L_2$ of the cord 30. Ends of the second subset of filaments 33b may be positioned adjacent to, overlapping and/or abutting the ends of the third subset of filaments 33c at the transition region 40. In some instances, the ends of the third subset of filaments 33c may be attached, affixed or bonded to the ends of the second subset of filaments 33b prior to intermingling the filaments 33 to form the cord 30. In other instances, the ends of the third subset of filaments 33c may remain unattached, unaffixed or unbonded to the ends of the second subset of filaments 33b throughout intermingling the filaments 33 to form the cord 30.

In some instances the transition region 40 may be subjected to additional processing to strengthen, reinforce or otherwise enhance the transition region 40 after forming the cord 30 with the braiding machine 100. For instance, as shown in FIG. 3C, the transition region 40 may be welded, such as by laser welding or ultrasonic welding, to strengthen the bond of the filaments 33 of the cord 30 in the transition region 40. For instance laser or ultrasonic welding may melt portions of the filaments 33, causing the filaments 33 to bond together. Other heat bonding means, such as local thermal welding, may also be used to bond the filaments 33 of the cord 30 in the transition region 40. Adhesive or solvent may also be used to bond the filaments 33 together in the transition region 40. In other embodiments, a collar (not shown) may be crimped, clamped, swaged, bonded, or otherwise coupled around the transition region 40 of the cord 30 to enhance the transition between the filaments 33 of the cord 30.

FIGS. 4A-4D illustrate an exemplary method of installing the vertebral stabilization system 10 of FIG. 1. The first vertebral anchor 12a may be installed on a first vertebra V1, the second vertebral anchor 12b may be installed on a second vertebra V2, and the third vertebral anchor 12c may be installed on a third vertebra V3.

With the vertebral anchors 12a, 12b, 12c secured to the vertebrae, the stabilization constructs 22a, 22b may be coupled to the vertebral anchors 12a, 12b, 12c. For example, as shown in FIG. 4A, the cord 30 may first be coupled to the head portion 14 of the second vertebral anchor 12b with the transition region 40 positioned in the channel of the head portion 14 of the second vertebral anchor 12b. A securing element, such as the threaded fastener 20 may be engaged with the head portion 14 to secure the cord 30 to the second vertebral anchor 12b.

Figure 4B:
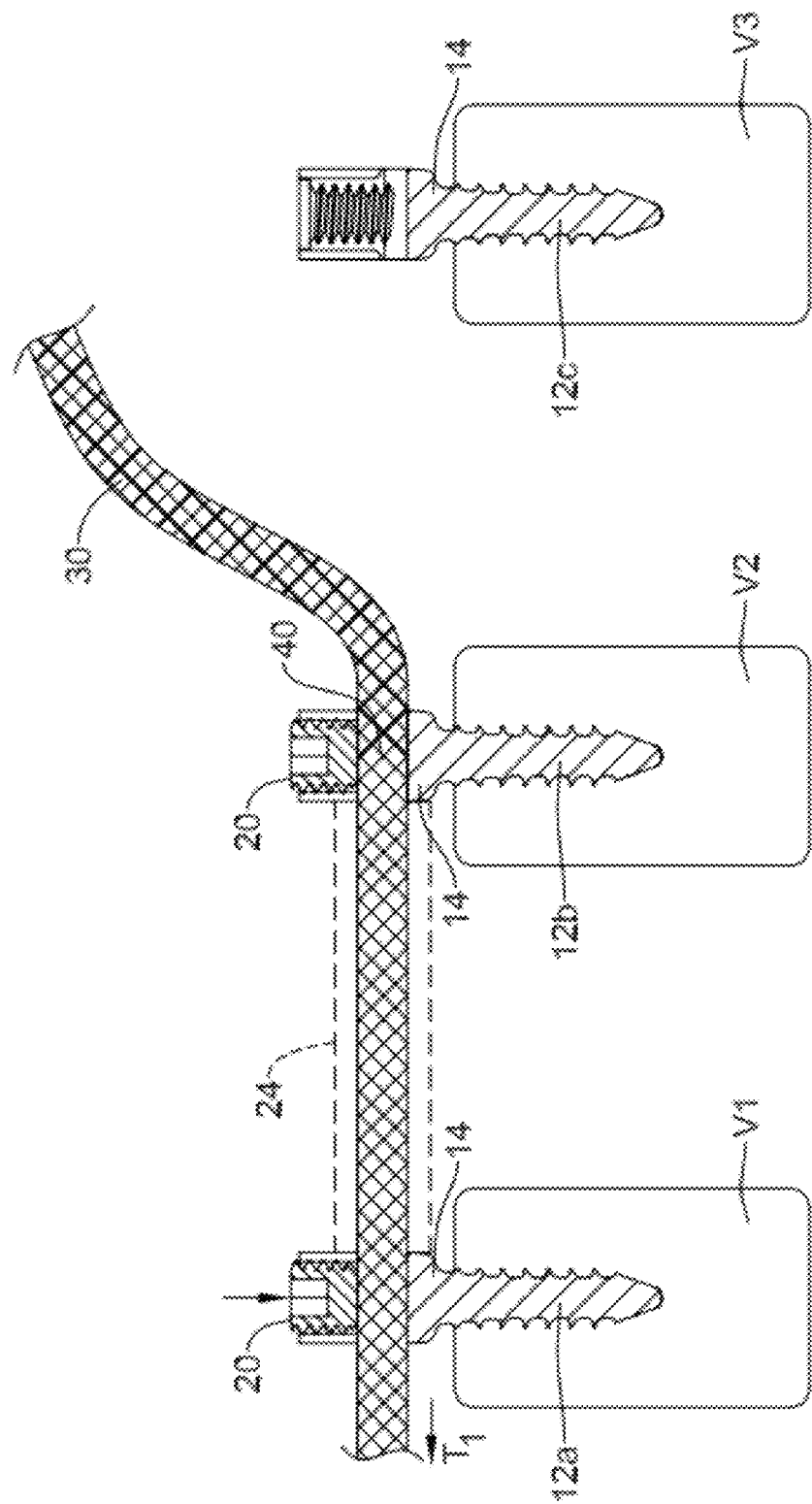

As shown in FIG. 4B, a spacer 24, disposed over the first length $L_1$ of the cord 30, may then be positioned between the head portion 14 of the first vertebral anchor 12a and the head portion 14 of the second vertebral anchor 12b, with the cord 30 extending through the channel of the first vertebral anchor 12a. A first amount of tension $T_1$ may be applied to the first length $L_1$, and the cord 30 may be coupled to the head portion 14 of the first vertebral anchor 12a while maintaining the first amount of tension $T_1$ on the first length $L_1$ of the cord 30. For instance, a securing element, such as a threaded fastener 20, may be engaged with the head portion 14 to secure the cord 30 to the first vertebral anchor 12a while the first length $L_1$ of the cord 30 between the head portion 14 of the first vertebral anchor 12a and the head portion 14 of the second vertebral anchor 12b is tensioned a first amount $T_1$.

Figure 4C:
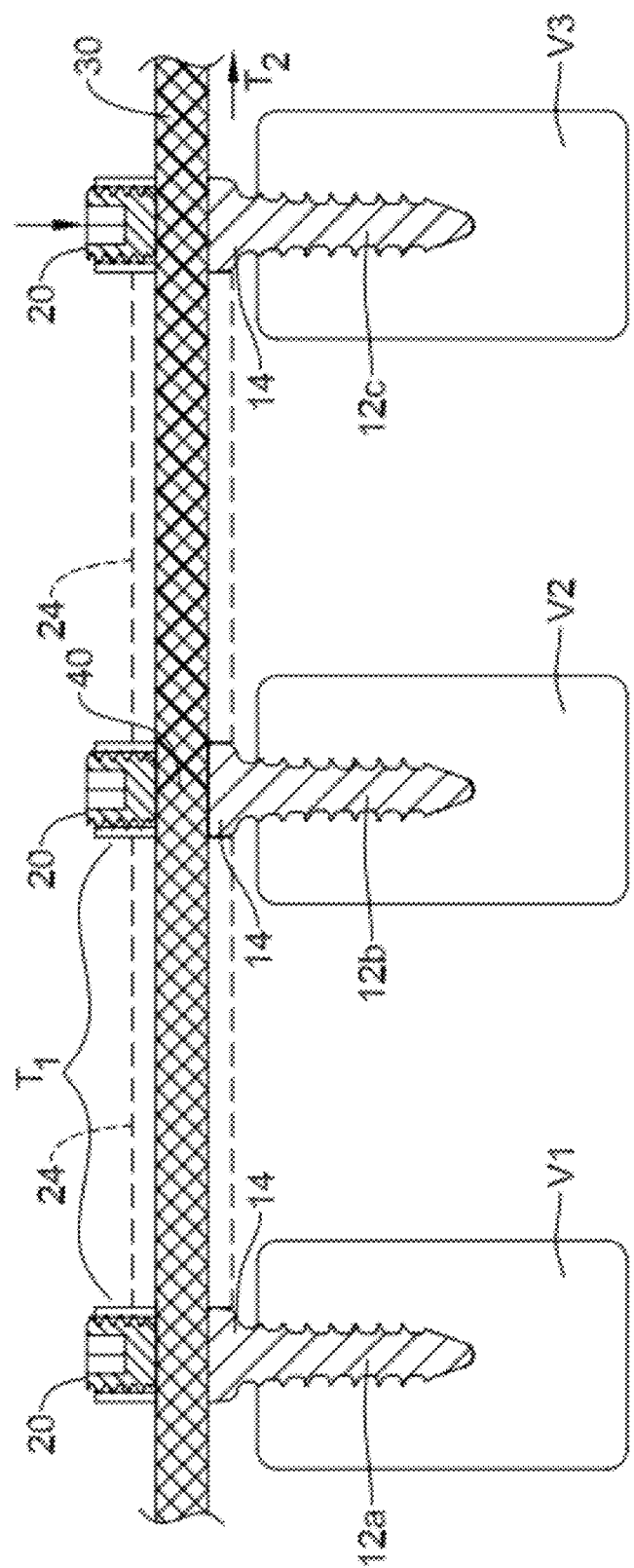

Additionally, as shown in FIG. 4C, a spacer 24, disposed over the second length $L_2$ of the cord 30, may then be positioned between the head portion 14 of the second vertebral anchor 12b and the head portion 14 of the third vertebral anchor 12c, with the cord 30 extending through the channel of the third vertebral anchor 12c. While maintaining the first amount of tension $T_1$ in the first length $L_1$ of the cord, a second amount of tension $T_2$ may be applied to the second length $L_2$, and the cord 30 may be coupled to the head portion 14 of the third vertebral anchor 12c while maintaining a second amount of tension $T_2$ on the second length $L_2$ of the cord 30. For instance, a securing element, such as a threaded fastener 20, may be engaged with the head portion 14 to secure the cord 30 to the third vertebral anchor 12c while second length $L_2$ of the cord 30 between the head portion 14 of the second vertebral anchor 12b and the head portion 14 of the third vertebral anchor 12c is tensioned a second amount $T_2$ and the first length $L_1$ of the cord 30 maintains the first amount of tension $T_1$.

Figure 4D:
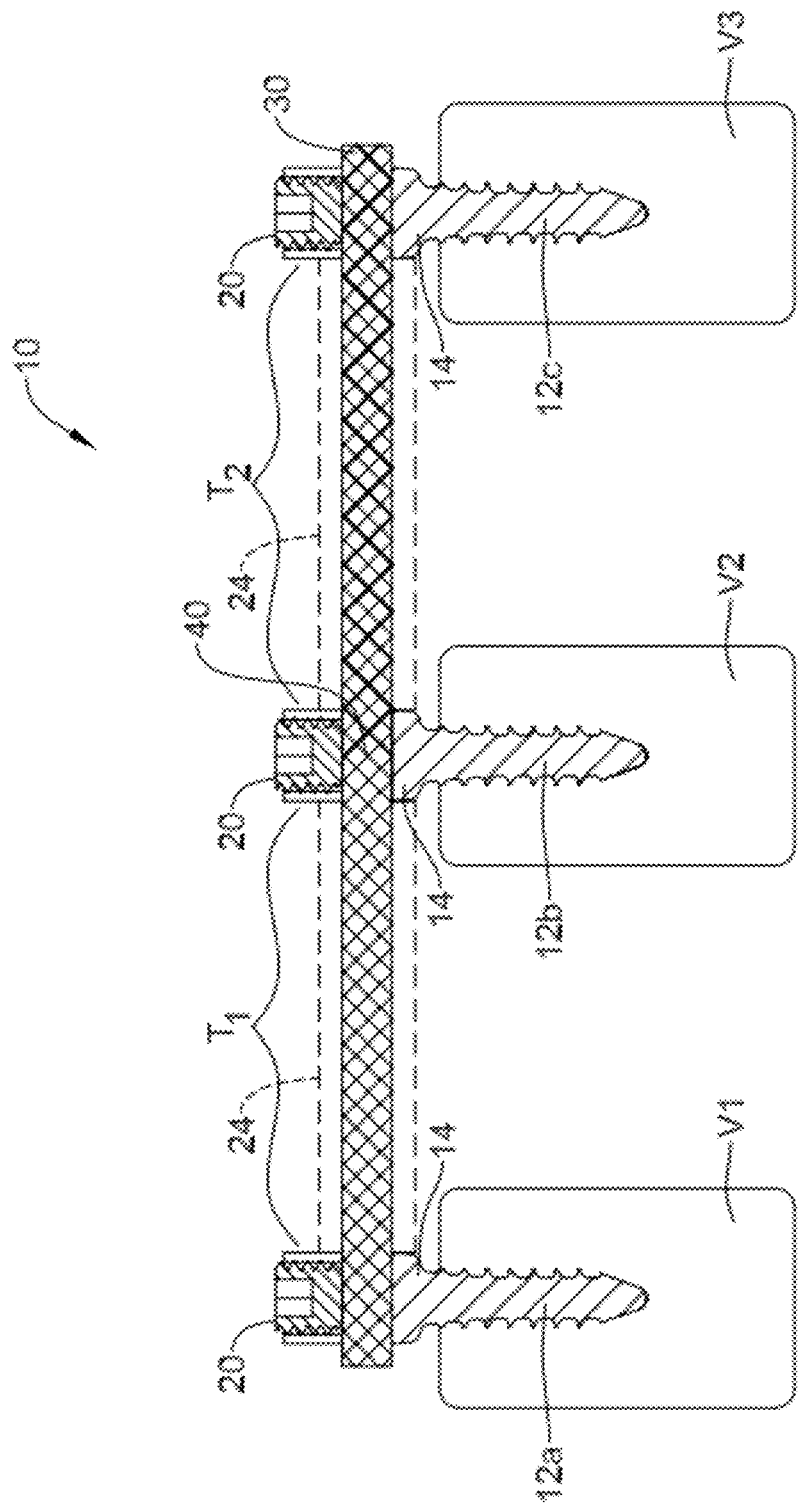

The assembled vertebral stabilization system 10 is shown in FIG. 4D in cross-section. When assembled, the first length $L_1$ of the cord 30 may be tensioned a first amount $T_1$ and the second length $L_2$ of the cord 30 may be tensioned a second amount $T_2$. The first amount of tension $T_1$ may be the same as or different from the second amount of tension $T_2$. The first amount of tension $T_1$ may be different from the second amount of tension $T_2$ to customize the vertebral stabilization system 10 at different vertebral levels for a given application. Thus, different portions of the cord 30 may be tensioned intraoperatively to a desired amount of tension independent of other portions of the cord 30, thereby providing a desired amount of tension at each spinal segment according to its pathology. The characteristics of the first length $L_1$ of the cord 30, being different from the characteristics of the second length $L_2$ of the cord 30, may also accommodate variations of the pathology of contiguous spinal segments. In some instances, the first amount of tension $T_1$ may vary by 5% or more, 10% or more, 20% or more, or 30% or more from the second amount of tension $T_2$ of the cord 30.

In other instances, the stabilization constructs 22 may be preassembled such that the cord 30 is pretensioned prior to coupling the stabilization constructs to the vertebral anchors 12a, 12b, 12c. For instance, the first length of the cord 30 may be tensioned a first amount $T_1$ and the second length of the cord 30 may be tensioned a second amount $T_2$ exterior of a patient, and then the preassembled constructs may be coupled to the previously installed vertebral anchors 12a, 12b, 12c.

FIGS. 5A-5E illustrate an exemplary method of installing another vertebral stabilization construct 210 on a portion of a spinal column. The first vertebral anchor 12a may be installed on a first vertebra V1, the second vertebral anchor 12b may be installed on a second vertebra V2, the third vertebral anchor 12c may be installed on a third vertebra V3, and the fourth vertebral anchor 12d may be installed on a fourth vertebra V4.

With the vertebral anchors 12a, 12b, 12c, 12d secured to the vertebrae, stabilization constructs may be coupled to the vertebral anchors 12a, 12b, 12c, 12d. For instance, a cord 230 may be positioned in the channels of the head portions 14 of the vertebral anchors 12a, 12b, 12c, 12d with spacers 24 positioned between the head portions 14 of adjacent vertebral anchors 12a, 12b, 12c, 12d. The cord 230, in some instances, may be similar to the cord 30 described above having multiple portions of different structural characteristics, or the cord 230 may be similar to the cords described in U.S. application Ser. No. 12/327,710, filed Dec. 3, 2008, entitled "Cord for Vertebral Fixation Having Multiple Stiffness Phases", incorporated herein by reference, in which case the cord 230 could have a variable stiffness depending on the amount of tension applied to the cord 230.

As shown in FIG. 5A, the cord 230 may be coupled to the head portion 14 of the first vertebral anchor 12a, such as with a threaded fastener 20, or other securing element. With the cord 230 secured to the first vertebral anchor 12a, a tensioning tool 250 may be used to apply a first amount of tension $T_1$ to the cord 230. The tensioning tool 250 may be any desired tool for tensioning the cord 230. For example, in some instances the tensioning tool 250 may be similar to the tensioning devices disclosed in U.S. Pat. No. 6,616,667 or U.S. Pat. App. Pub. No. 2008/0009863, each of which is incorporated herein by reference. The tensioning tool 250 may be equipped with a means for measuring the amount of tension applied to the cord 230. For instance, the tensioning tool 250 may include a sensor, gauge, or meter to measure the applied force in a continuous real-time manner, or otherwise.

As shown in FIG. 5B, a securing element, such as a threaded fastener 20, may be engaged with the head portion 14 of the second vertebral anchor 12b to secure the cord 230 to the second vertebral anchor 12b while the first amount of tension $T_1$ is applied to the cord 230. Thus, the first amount of tension $T_1$ may be applied to the cord 230 from the head portion 14 of the first vertebral anchor 12a to the tensioning tool 250.

While the first amount of tension $T_1$ is maintained in a first portion of the cord 230 between the first vertebral anchor 12a and the second vertebral anchor 12b, the tensioning tool 250 may be used to apply a second amount of tension $T_2$ to the cord 230 extending from the head portion 14 of the second vertebral anchor 12b. As shown in FIG. 5C, a securing element, such as a threaded fastener 20, may be engaged with the head portion 14 of the third vertebral anchor 12c to secure the cord 230 to the third vertebral anchor 12c while the second amount of tension $T_2$ is applied to a second portion of the cord 230 between the second vertebral anchor 12b and the third vertebral anchor 12c. Thus, the second amount of tension $T_2$ may be applied to the cord 230 from the head portion 14 of the second vertebral anchor 12b to the tensioning tool 250.

Figure 5D:
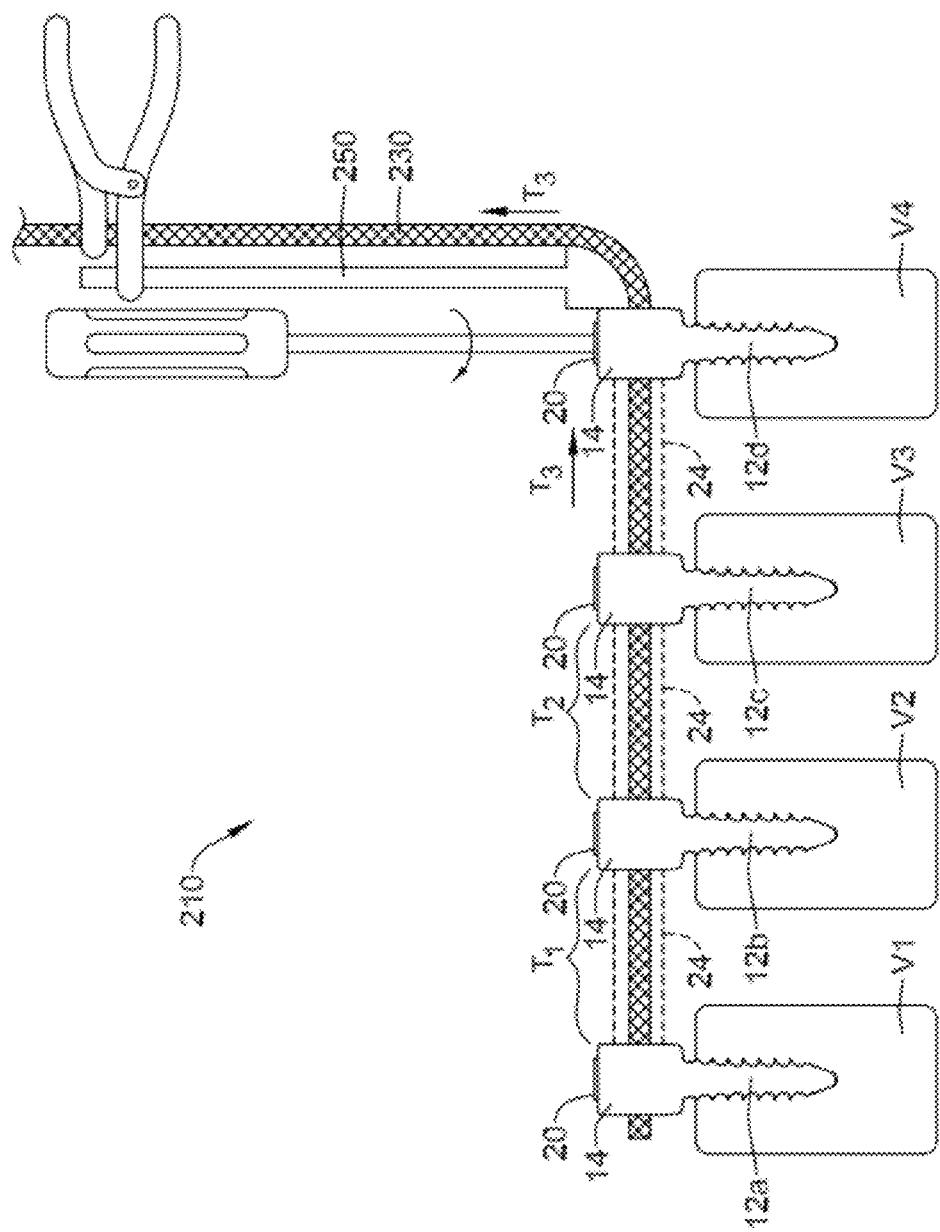

While the first amount of tension $T_1$ is maintained in the first portion of the cord 230 between the first vertebral anchor 12a and the second vertebral anchor 12b and the second amount of tension $T_2$ is maintained in the second portion of the cord 230 between the second vertebral anchor 12b and the third vertebral anchor 12c, the tensioning tool 250 may be used to apply a third amount of tension $T_3$ to the cord 230 extending from the head portion 14 of the third vertebral anchor 12c. As shown in FIG. 5D, a securing element, such as a threaded fastener 20, may be engaged with the head portion 14 of the fourth vertebral anchor 12d to secure the cord 230 to the forth vertebral anchor 12d while the third amount of tension $T_3$ is applied to a third portion of the cord 230 between the third vertebral anchor 12c and the fourth vertebral anchor 12d. Thus, the third amount of tension $T_3$ may be applied to the cord 230 from the head portion of the third vertebral anchor 12c to the tensioning tool 250.

Once the desired amount of tension is individually applied to each portion of the cord 230 at each spinal segment, excess portions of the cord 230 may be trimmed away. As shown in FIG. 5E, the assembled vertebral stabilization system 210 is assembled such that a first portion of the cord 230 between the head portions 14 of the first and second vertebral anchors 12a, 12b has a first amount of tension $T_1$, a second portion of the cord 230 between the head portions 14 of the second and third vertebral anchors 12b, 12c has a second amount of tension $T_2$, and a third portion of the cord 230 between the head portions 14 of the third and fourth vertebral anchors 12c, 12d has a third amount of tension $T_3$.

The first amount of tension $T_1$, the second amount of tension $T_2$, and/or the third amount of tension $T_3$ may be different from one or more of the other amounts of tension applied to the cord 230 to customize the vertebral stabilization system 210 at different vertebral levels for a given application. Thus, different portions of the cord 230 may be tensioned intraoperatively to a desired amount of tension independent of other portions of the cord 230, thereby providing a desired amount of tension at each spinal segment according to its pathology.

The characteristics of the first portion of the cord 230, being different from the characteristics of the second portion of the cord 30, may also accommodate variations of the pathology of contiguous spinal segments. For instance, in the event that the cord 230 had variable stiffness such as the cord disclosed in U.S. application Ser. No. 12/327,710, then, the first portion, the second portion and/or the third portion of the cord 230 may be stiffer than one or more other portions of the cord 230 depending on the amount of tension applied to a given portion of the cord 230. In some instances, the first amount of tension $T_1$, the second amount of tension $T_2$, and/or the third amount of tension $T_3$ may vary by 5% or more, 10% or more, 20% or more, or 30% or more from another portion of the cord 230.

Although the cord designs discussed herein have been illustrated with a circular cross-section, it is noted that in some embodiments it may be possible and/or desirable to provide the cord designs with a non-circular cross-section. For instance, tape, ribbon, rectangular, triangular, elliptical, as well as other regular or irregular cross-sectional geometries are possible.

Although the cord designs discussed herein have been illustrated as a component of a pedicle-based spinal stabilization system, the cord designs may also be incorporated into other spinal stabilization systems. For example, the cord designs could be used with an interspinous process spacer such as disclosed in U.S. Pat. Nos. 6,761,720, 6,946,000, 7,163,558 and 7,238,204, each of which is incorporated herein by reference. Additionally, the cord designs could be used with a vertebral fixing system including a clamp which may be universally clamped to an elongate rod, such as the clamping construct disclosed in U.S. Pat. No. 7,481,828, incorporated herein by reference.

Those skilled in the art will recognize that the present invention may be manifested in a variety of forms other than the specific embodiments described and contemplated herein. For example, technologies described herein may be directed to various animal species, not necessarily limited to humans. Additionally, although technologies described herein have been discussed in regard to the spinal column, it is understood that they may also be applied in other medical applications, if desired. For example, it may be found advantageous to utilize a cord as described herein for tendon replacement, or other desired applications. Accordingly, departure in form and detail may be made without departing from the scope and spirit of the present invention as described in the appended claims.

What is claimed is:

1. A spinal stabilization system comprising:
   a first vertebral anchor configured to be secured to a first vertebra;
   a second vertebral anchor configured to be secured to a second vertebra;
   a third vertebral anchor configured to be secured to a third vertebra; and
   a cord extendable between the first, second and third vertebral anchors, a first length of the cord including a first set of intermingled filaments, and a second length of the cord including a second set of intermingled filaments;
   wherein the first set of intermingled filaments includes a first subset of filaments and a second subset of filaments, and the second set of intermingled filaments includes the first subset of filaments of the first set of intermingled filaments and a third subset of filaments of a material different than a material of the second subset of filaments of the first set of intermingled filaments;
   wherein the cord includes a transition region between the first length of the cord and the second length of the cord;
   wherein the transition region is a region where ends of the second subset of filaments and ends of the third subset of filaments are located; and
   wherein the ends of the second subset of filaments at the transition region are adjacent to the ends of the third subset of filaments at the transition region.

2. The spinal stabilization system of claim 1, wherein the transition region of the cord is positioned at the second vertebral anchor such that the first length of the cord extends between the second vertebral anchor and the first vertebral anchor and the second length of the cord extends between the second vertebral anchor and the third vertebral anchor.

3. The spinal stabilization system of claim 1, wherein the first length of the cord has a first amount of elongation per unit of applied tensile force and the second length of the cord has a second amount of elongation per unit of applied tensile force different from the first amount of elongation per unit of applied tensile force.

4. The spinal stabilization system of claim 1, wherein the first length of the cord has a first stiffness and the second length of the cord has a second stiffness different from the first stiffness.

5. A method of forming a cord for a spinal stabilization system, the method comprising:
   forming a first length of a cord by braiding a first subset of filaments with a second subset of filaments;
   substituting the second subset of filaments with a third subset of filaments having an elasticity different than an elasticity of the second subset of filaments after the first length of the cord is formed;
   forming a second length of the cord by braiding the first subset of filaments with the third subset of filaments;
   substituting at least a portion of the third subset of filaments with a fourth subset of filaments different from the third subset of filaments after the second length of the cord is formed; and
   forming a third length of the cord by braiding the first subset of filaments with the fourth subset of filaments.

6. The method of claim 5, further comprising:
   applying laser energy to a transition region of the cord between the first length and the second length of the cord to enhance the transition region between the second subset of filaments to the third subset of filaments.

7. The method of claim 5, further comprising:
   applying ultrasonic energy to a transition region of the cord between the first length and the second length of the cord to enhance the transition region between the second subset of filaments to the third subset of filaments.

8. A spinal stabilization system comprising:
   a first vertebral anchor configured to be secured to a first vertebra;
   a second vertebral anchor configured to be secured to a second vertebra;
   a third vertebral anchor configured to be secured to a third vertebra; and
   a cord extendable between the first, second and third vertebral anchors, a first length of the cord including a first set of intermingled filaments, and a second length of the cord including a second set of intermingled filaments;
   wherein the first set of intermingled filaments includes a first subset of filaments and a second subset of filaments, and the second set of intermingled filaments includes the first subset of filaments of the first set of intermingled filaments and a third subset of filaments different from the second subset of filaments of the first set of intermingled filaments;

wherein the cord includes a transition region between the first length of the cord and the second length of the cord;

wherein the transition region is a region where ends of the second subset of filaments and the ends of the third subset of filaments are located; and wherein the ends of the second subset of filaments at the transition region are adjacent to the ends of the third subset of filaments at the transition region.

9. A method of forming a cord for a spinal stabilization system, the method comprising:

forming a first length of a cord by braiding a first subset of filaments with a second subset of filaments;

substituting the second subset of filaments with a third subset of filaments different from the second subset of filaments after the first length of the cord is formed;

forming a second length of the cord by braiding the first subset of filaments with the third subset of filaments;

substituting at least a portion of the third subset of filaments with a fourth subset of filaments different from the third subset of filaments after the second length of the cord is formed; and forming a third length of the cord by braiding the first subset of filaments with the fourth subset of filaments.

* * * * *